(12) United States Patent
Willson, III et al.

(10) Patent No.: US 7,893,222 B2
(45) Date of Patent: *Feb. 22, 2011

(54) INTRODUCTION OF STRUCTURAL AFFINITY HANDLES AS A TOOL IN SELECTIVE NUCLEIC ACID SEPARATIONS

(75) Inventors: Richard Coale Willson, III, Houston, TX (US); Luis Antonio Cano, Houston, TX (US)

(73) Assignees: University of Houston, Houston, TX (US); Technology Licensing Co. LLC, Palm Harbor, FL (US)

( * ) Notice: Subject to any disclaimer, the term of this patent is extended or adjusted under 35 U.S.C. 154(b) by 1021 days.

This patent is subject to a terminal disclaimer.

(21) Appl. No.: 10/737,403

(22) Filed: Dec. 16, 2003

(65) Prior Publication Data

US 2006/0160093 A1    Jul. 20, 2006

Related U.S. Application Data

(60) Provisional application No. 60/434,901, filed on Dec. 20, 2002.

(51) Int. Cl.
*A23J 1/00* (2006.01)

(52) U.S. Cl. ........................ 530/415; 530/412
(58) Field of Classification Search ............ None
See application file for complete search history.

(56) References Cited

U.S. PATENT DOCUMENTS

| | | | | |
|---|---|---|---|---|
| 5,296,467 A * | 3/1994 | Reutelingsperger | .......... | 514/12 |
| 5,843,654 A * | 12/1998 | Heisler et al. | .................. | 435/6 |
| 5,898,071 A * | 4/1999 | Hawkins | .................... | 536/25.4 |
| 5,945,522 A * | 8/1999 | Cohen et al. | ................ | 536/23.1 |
| 5,948,646 A * | 9/1999 | Srivastava | .................. | 435/69.3 |
| 2001/0055780 A1 * | 12/2001 | Cherwonogrodzky et al. | .......................... | 435/7.32 |
| 2004/0152076 A1 * | 8/2004 | Willson et al. | .................. | 435/6 |

FOREIGN PATENT DOCUMENTS

WO   WO 9800435 A2 *  1/1998
WO   WO 0246398 A2 *  6/2002

OTHER PUBLICATIONS

Pham et al. Preparation of pure plasmid or cosmid DNA using single-strand affinity matrix and gel-filtration spin columns. BioTechniques, vol. 20, No. 3, pp. 492-497 (1996).*
Colman et al. Rapid purification of plasmid DNAs by hydroxyapatite chromatography. Eur. J. Biochem. 91:303-310 (1978).*
Birnboim et al. A rapid alkaline extraction procedure for screening recombinant plasmid DNA. Nucleic Acids Research 7(6):1513-1523 (1979).*

* cited by examiner

*Primary Examiner*—Samuel C Woolwine
(74) *Attorney, Agent, or Firm*—Richard Coale Willson, Jr.

(57) ABSTRACT

The method is used for separating nucleic acids and other similar constructs. It involves selective introduction, enhancement, or stabilization of affinity handles such as single-strandedness in the undesired (or desired) nucleic acids as compared to the usual structure (e.g., double-strandedness) of the desired (or undesired) nucleic acids. The undesired (or desired) nucleic acids are separated from the desired (or undesired) nucleic acids due to capture by methods including but not limited to immobilized metal affinity chromatography, immobilized single-stranded DNA binding (SSB) protein, and immobilized oligonucleotides. The invention is useful to: remove contaminating genomic DNA from plasmid DNA; remove genomic DNA from plasmids, BACs, and similar constructs; selectively separate oligonucleotides and similar DNA fragments from their partner strands; purification of aptamers, (deoxy)-ribozymes and other highly structured nucleic acids; Separation of restriction fragments without using agarose gels; manufacture recombinant Taq polymerase or similar products that are sensitive to host genomic DNA contamination; and other applications.

12 Claims, 4 Drawing Sheets

Figure 1: **Removal of *E. coli* genomic DNA from pCMVsport-β-gal**

Figure 2: Predicted Secondary Structure of anti-VEGF aptamer
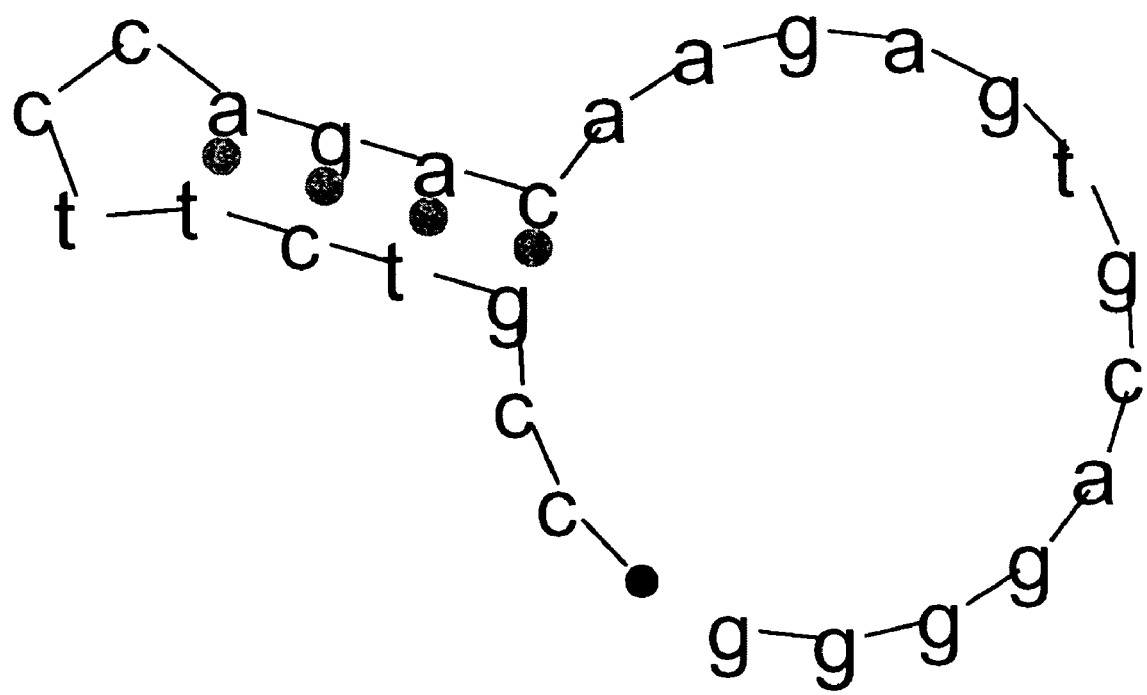

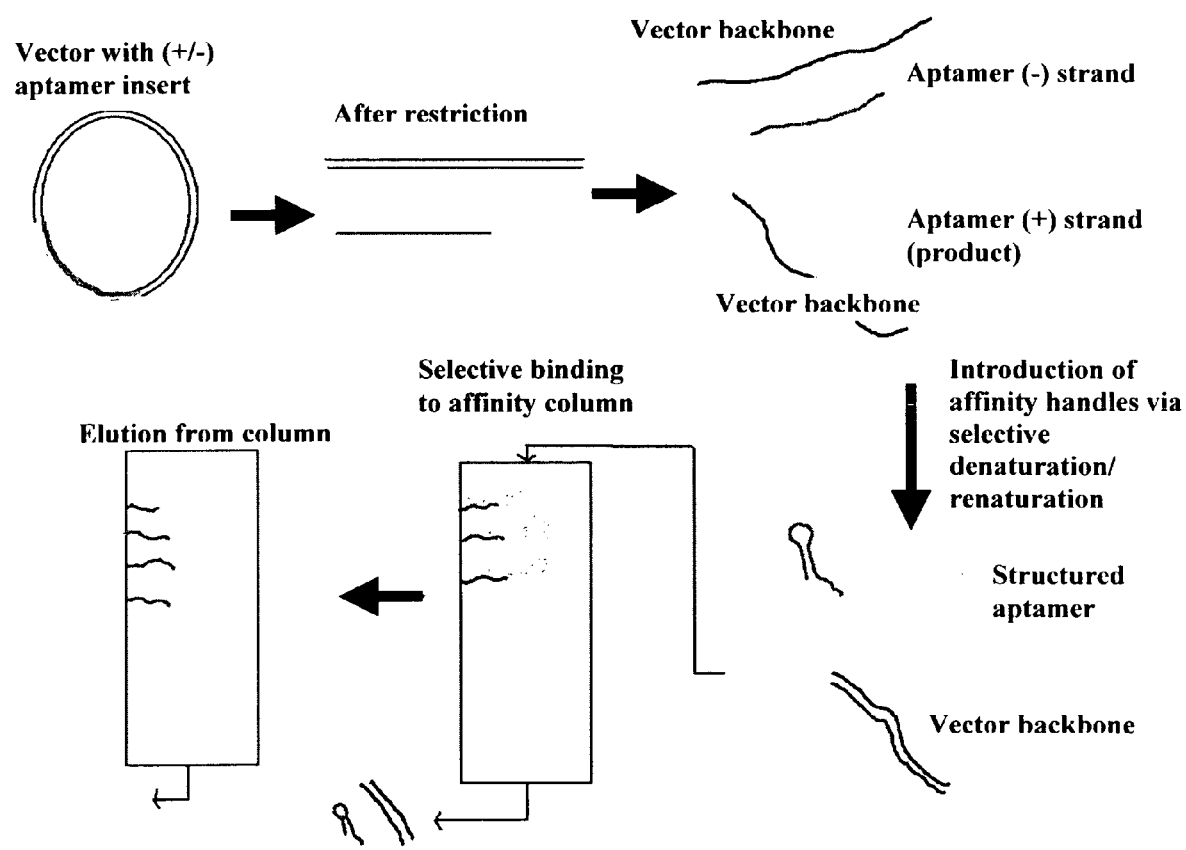
Figure 3: Graphical Representation of Aptamer Purification Using Introduction of Affinity Handles Followed by Affinity Capture

Figure 4: General Purification Scheme for Introduction of Affinity Handles Followed by Affinity Capture Using Heating and Quenching Followed by an Affinity Column
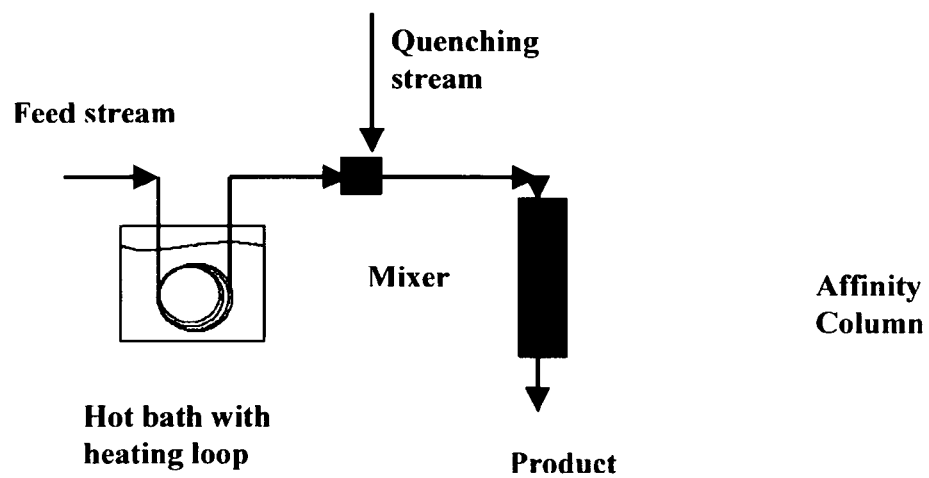
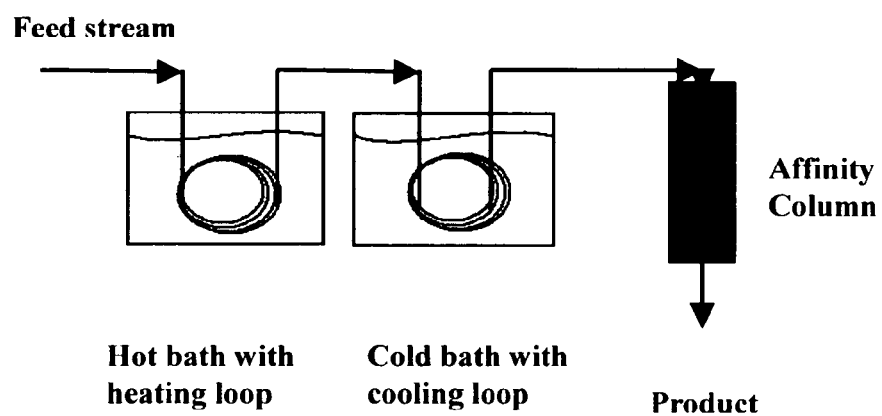

INTRODUCTION OF STRUCTURAL AFFINITY HANDLES AS A TOOL IN SELECTIVE NUCLEIC ACID SEPARATIONS

The present application claims priority of provisional U.S. Ser. No. 60/434,901 filed 20 Dec. 2002.

STATEMENT REGARDING FEDERALLY SPONSORED RESEARCH OR DEVELOPMENT

This invention was made with government support under Cooperative Agreement NCC 9-58 awarded by NASA. The government has certain rights in the invention.

BACKGROUND OF THE INVENTION

1. Field of the Invention

The present invention relates to the general field of biochemical separations, generally classified in U.S. Patent Class 435.

2. Description of the Prior Art

Advances in gene therapy, DNA vaccines and other DNA-based therapeutics have increased the demand for large-scale production of plasmid DNA and other circular constructs such as bacterial artificial chromosomes (BACs) that are relatively free of contaminants. In gene therapy, plasmid DNA-based vectors are preferred over viral-based vectors because they lack the issues specific to the viral vectors, such as the difficulties with producing and purifying high viral titers, viral vector-related toxicity, the possibility of insertion into the human genome, and potential reversion to active viruses. As these areas progress, there will be an increasing need for large-scale production of these constructs in their efficacious form that are free of genomic DNA and other contaminants like irreversibly denatured plasmid and relaxed or nicked plasmid isoforms. At least one investigator at the U.S. Food and Drug Administration (FDA) has recommended a level of no more than 10 nanograms of genomic DNA per human dose for pharmaceutical grade DNA vaccines.

Genomic DNA contamination also can impair processes used in the laboratory and in industry. For example, such contamination can inhibit or obstruct polymerase chain reaction (PCR) and sequencing reactions.

Several methods exist for the separation of DNA and other nucleic acids, such as ion exchange chromatography, adsorption onto silica or glass beads in the presence of chaotropic ions, electrostatic interaction with DEAE-cellulose membrane paper, ligand exchange on metal-loaded cation exchange resin, hydrophobic interaction chromatography, hydroxyapatite adsorption, immobilized oligonucleotides, and size exclusion chromatography (SEC).

Specific prior publications known to the inventors include
(1) Murphy, J. C.; Wibbenmeyer, J. A.; Fox, G. E.; Willson, R. C. *Nat Biotechnol* 1999, 17, 822-823. (Does not include selective Denaturation/Renaturation prior to IMAC binding)
(2) Prazeres, D. M.; Ferreira, G. N.; Monteiro, G. A.; Cooney, C. L.; Cabral, J. M. *Trends Biotechnol* 1999, 17, 169-174. Birnboim, H. C. *Methods Enzymol* 1983, 100, 243-255. (Does not include the use of selective denaturation for changing the conformational state of gDNA to allow selective sep. from plasmid DNA)
(3) Wetmur, J. G.; Davidson, N. *J Mol Biol* 1968, 31, 349-370. (Does not utilize the denatured DNA affinity handles)
(4) Marmur, J.; Doty, P. *Journal of Molecular Biology* 1961, 3, 585-594. (Does not include the use of selective renaturation for purification)
(5) Viglasky, V.; Antalik, M.; Adamcik, J.; Podhradsky, D. *Nucleic Acids Res* 2000, 28, E51. (does not include the use of conformational stability of plasmid DNA in selective denaturation/renaturation of genomic DNA in the presence of plasmid)
(6) Willson, R. C.; Murphy, J. C. WO 02/46398 A2, published Jun. 13, 2002. (Does not include selective denaturation prior to binding)
(7) Bridonneau, P. B., Seve; Tengler, Robert; Hill, Ken; Carter, Jeff; Pieken, Wolfgang; Tinnermeier, David; Lehrman, Russ; Drolet, Daniel W.; *Journal of Chromatography, B* 1999, 726, 237-247. (Denaturing conditions are used only to disrupt secondary structure, not to utilize it)
(8) Deregon, J. M. S., Daniel; Mitchell, Grant; Potier, Michel; Labuda, Damian *Nucleic Acids Research* 1990, 18, 6149. (Does not use any type of affinity method, for the removal of gDNA prior to PCR)
(9) Lima, W. F. *American Biotechnology Laboratory* 1988, 6, 20-22. (Uses the method of alkaline lysis to remove linear and open-circle DNA, does not use selective affinity methods)

None of the above references is understood to teach the steps of introducing affinity handles into certain desired (or undesired) moieties, then using these handles to separate out desired (or undesired) moieties.

3. Problems Presented by Prior Art

While there are several methods for separating DNA and other nucleic acids, these techniques either lack appropriate selectivity or desired capacity. For example, in the case of genomic DNA removal, some separation methods, such as hydroxyapatite adsorption or immobilized oligonucleotides, do not readily achieve the selectivity needed to separate genomic DNA from chemically similar plasmid DNA, or may be too sequence specific to be generally applicable.

Other methods are only suitable for producing small amounts of the desired nucleic acids. Anion exchangers have difficulty separating plasmid DNA from genomic DNA fragments of similar affinity, and also generally have a low capacity for nucleic acids. SEC has the disadvantages of low capacity and dilution of the sample, leading to lower yields. SEC also cannot easily remove genomic DNA fragments of a broad size distribution, which could lead to the unwanted co-elution of contaminant with the desired product.

These methods fail to achieve the necessary selectivity for more general separations such as oligonucleotide separations, aptamer purification, restriction fragment isolation, and other separations involving similar chemical species.

There is a need for a more selective method of separating plasmid DNA or similar constructs from genomic DNA that results in a relatively uncontaminated product in larger volumes and yields than achieved with current separation methods. There is also a need for nucleic acid separations that attain a selectivity that is not available with current methods. These separations that require higher selectivity include aptamer purification, separation of complementary strands of DNA (one of which may be a functional DNA; e.g. aptamer, deoxyribozyme), and rapid separation of restriction fragments that are non gel-based.

SUMMARY OF THE INVENTION

Current methods for separating nucleic acids either lack sufficient selectivity or large capacity production as required for gene therapy or DNA vaccines or other applications. There is a need for a more selective method of separating nucleic acids that results in a relatively uncontaminated product in larger volumes and yields than achieved with currently available separation methods.

The novel separation technique described herein addresses these shortcomings. This method, which extends to, but is not limited to a number of alternative structures and chemistries for nucleic acids (for example, alternative backbone structures), involves the selective introduction, enhancement, stabilization of structural "affinity handles" such as single-strandedness in the undesired (or desired) nucleic acids as compared to the usual structure, such as double-strandedness, of the desired (or undesired) nucleic acids. The exposed bases of single-stranded undesired (or desired) nucleic acids allow capture of the undesired (or desired) nucleic acids by techniques which are selective for single stranded regions of nucleic acids, such as but not limited to immobilized metal affinity chromatography (IMAC), hydrophobic interaction chromatography (HIC), reversed-phase chromatography (RPC), immobilized single-stranded DNA binding (SSB) protein, immobilized nucleic acids (poly-dT, poly-dU, or specific sequences), or the use of peptide nucleic acids (PNAs). We have shown that IMAC can selectively and efficiently capture nucleic acids containing exposed purine bases and separate them from the desired product. We have shown that this method of introduction of affinity handles followed by capture can be used to remove contaminating E. coli genomic DNA from supercoiled plasmid. It can also remove other circular constructs that are on a smaller order of size than, for example, E. coli genomic DNA. Unlike anion exchangers, only the trace contaminant is bound and the effective capacity for the desired product is high.

Processes such as selective thermal denaturation and renaturation, alkaline denaturation, the use of restriction enzymes yielding single-stranded overhangs, the use of oligonucleotide dTs, single-stranded DNA binding proteins, minerals, and the use of primers or other nucleic acid fragments such as complementary DNA are useful for introducing, enhancing, or stabilizing affinity handles (e.g., single strandedness) in the undesired (or desired) nucleic acids to facilitate capture and separation of the undesired (or desired) nucleic acid from the desired (or undesired) nucleic acids, carbohydrate or protein.

This technique can be used to remove unwanted nucleic acid sequences that are already single-stranded, such as irreversibly denatured plasmids that have lost their supercoiled nature or other nucleic acid fragments, and enhance the purification of the favored nucleic acid product or other product.

This novel separation method can be easily scaled up for production of larger yields.

Any combination of techniques for introducing, stabilizing, or enhancing affinity handles and capturing the separated results, which includes a variety of products, can be used. One implementation of selective separation of nucleic acids uses selective thermal denaturation and renaturation followed by capture (e.g., by IMAC or other methods like immobilized nucleic acids). Another implementation uses pH or other chemical denaturation followed by capture (e.g., by IMAC). This invention may be used to separate genomic DNA from plasmid DNA or other circular constructs; to separate oligonucleotides (and other similar nucleic acid fragments) from their partner strands; to purify aptamers and other functional nucleic acids from restriction fragments, PCR products, and other DNA sources; or to purify proteins, carbohydrates or other products from nucleic acids such as genomic DNA.

DETAILED DESCRIPTION OF INVENTION

In contrast to proteins, nucleic acids can tolerate reversible modification of their conformations. This separation method can take advantage of this characteristic of nucleic acids and permits higher selectivity than would otherwise be achieved.

One implementation of selective separation of nucleic acids uses selective renaturation with capture (e.g., capture with IMAC) to remove contaminating genomic DNA from plasmid DNA. Plasmid DNA quickly renatures after denaturation and rapid cooling while genomic DNA remains partially denatured upon rapid cooling. This partially denatured state for genomic DNA is enhanced and stabilized with high ionic strength buffer. A metal chelate matrix (IMAC) selectively binds partially denatured genomic DNA through its exposed purine bases; double-stranded renatured plasmid DNA is not bound. This separation method can attain an eight-log clearance of 30% E. coli genomic DNA (by weight) from samples containing the plasmid pCMVsport-β-gal.

Another implementation for this separation method uses alkaline denaturation, which is well suited for smaller laboratory-scale separations. Other techniques are described below in further detail.

Introducing Affinity Handles

Selective thermal denaturation and renaturation, alkaline denaturation and the use of restriction enzymes yielding single-stranded overhangs are all possible methods of introducing affinity handles. The resulting handles may be captured by the use of oligonucleotide dTs to capture single stranded regions, single-stranded DNA binding proteins, minerals, and the use of primers or other nucleic acid fragments such as complementary DNA nucleic acids. The introduced selectivity of affinity handles can facilitate capture and separation of the undesired (or desired) nucleic acid from the desired (or undesired) nucleic acids, such as open circular (nicked) and linear. The introduction of affinity handles may also be conveniently accomplished through other steps already incorporated into a process, such as heat-based or alkali-based microbial lysis of plasmid DNA. In the case of a heat-based process, the exiting stream can be rapidly cooled in order to form affinity handles on the contaminant (genomic DNA) and then be captured by a suitable affinity method as described below.

Selective Thermal Denaturation and Renaturation (e.g., for Genomic DNA Removal)

Selective capture of denatured genomic DNA (e.g., by IMAC) requires denaturation under conditions which either minimally or reversibly denatures plasmid in its desired form while converting genomic DNA into a form that can be adsorbed, particularly as the higher temperatures used to denature genomic DNA can adversely affect plasmid DNA's ability to renature in the desired form.

A three-step process can accomplish the desired separation. The sample is heated in a heating buffer with little salt (like sodium chloride) in the denaturation step. In the quenching step, the sample is renatured at a lower temperature in a quenching buffer that has higher ionic strength than the heating buffer. The unwanted nucleic acids are then separated by techniques like IMAC, which captures nucleic acids with single-stranded portions.

In the first step, heating denatures DNA, degrading genomic DNA in particular, in a buffer with low ionic strength or low salt concentration. Genomic DNA will denature at a much higher temperature than plasmid DNA. This higher denaturation temperature for genomic DNA can lead to high-temperature scission of the plasmid DNA and to unusable product. As nucleic acid melting temperature is strongly dependent on the ionic strength of the solvent, denaturation in low salt lowers genomic DNA melting temperature. The lower heating temperature minimizes damage to plasmid DNA from high-temperature scission.

The quenching step in a buffer with higher ionic strength kinetically traps the genomic DNA in a partially denatured state by stabilizing mismatched/non-specific base pairing. The plasmid DNA is basically unaffected and will renature substantially in its preferred supercoiled form. The higher ionic strength of the quenching buffer also promotes IMAC binding of the denatured genomic DNA in the next step.

In the last step, IMAC or other capture techniques remove the undesired genomic DNA, irreversibly denatured plasmid formed during heating, and traces of RNA. IMAC, presently the best means of capturing the undesired nucleic acids, selectively binds to exposed purine bases in partially denatured genomic DNA, separating it from double-stranded renatured plasmid DNA. A yield of about ninety percent (90%) recovery of the total plasmid DNA in its desired supercoiled form has been observed using IMAC. Other single/double-stranded selective methods also apply for capture such as hydroxyapatite adsorption or immobilized oligonucleotides.

The range of temperatures and heating time applicable to selective thermal denaturation and renaturation may vary, but the ideal temperatures are such that genomic DNA is effectively degraded and denatured while avoiding significant damage or irreversible denaturation for the desired nucleic acid sequences in their desired forms. In other words, one should operate in a temperature range above the melting temperature of linear DNA (genomic DNA in this implementation), but below the temperature for the late helix-coil transition of the plasmid, when the two strands of the plasmid molecule completely separate but are still topologically linked. One should avoid the temperature for the late helix-coil transition state for plasmid as it can lead to the formation of irreversibly denatured plasmid DNA upon cooling. This temperature range should also promote the desired denaturation of genomic DNA regardless of the initial state of the genomic DNA—namely, whether it is sheared as compared to intact.

The range of effective ionic strengths applicable for both heating and quenching buffers will vary. The desired ionic strength for the heating buffer should be sufficiently low so that the melting temperature of genomic DNA in question is reduced and the overall denaturation temperature can be lowered. At a lower denaturation temperature, high-temperature scission damage to plasmid DNA can be minimized during heating. The heating buffer should also be at an ionic strength that does not promote scission of plasmid DNA at low ionic strength. Similarly, the quenching buffer should be at an ionic strength higher than the heating buffer such that plasmid DNA renatures in its original form, but genomic DNA remains partially denatured with exposed bases. At some higher ionic strengths, binding of denatured genomic DNA to IMAC is also promoted.

Alkaline Denaturation

Similar results to the thermal heat/quench method have been achieved using an alkali denaturation scheme in conjunction with IMAC for selective separation. The results are similar to those derived from selective thermal denaturation and renaturation. This alkali method may be well suited to automation in small-scale, parallel operations, and closely resembles the familiar alkaline lysis method of addition of alkali solution followed by neutralization.

Other Affinity Handles

Structural forms such as Hairpins, Stems, Loops, Cruciforms, G quartets, single-stranded extensions and modifications to the phosphate backbone all constitute possible affinity handles for capture.

Other Vectors

Selective separation of nucleic acids can also be used to purify constructs other than supercoiled plasmid DNA. For example, the method of heating and quenching followed by IMAC can be used to remove genomic DNA from plasmids, BACs, and similar constructs, provided that the size of the construct is not on the order of the genome in question (e.g., E. Coli genomic DNA). The melting temperature of linear DNA is generally above the temperature for the early helix-coil transition in plasmids or other circular constructs, but below the temperature for the late helix-coil transition. One must only exceed the early helix-coil transition to effectively denature degraded/linearized genomic DNA. The early helix-coil transition is a function of a construct's superhelicity and is largely independent of size and sequence.

Other Applications:

Aptamer Purification and Separation of DNA Strands

The selective renaturation with capture technique can be used to selectively separate oligonucleotides and similar DNA fragments from their partner strands. In particular, this method can be used to purify aptamers, small interfering RNAs (siRNAs) and other functional DNAs from restriction fragments, PCR products, or other nucleic acid sources. After denaturation and rapid return to native conditions, a structured DNA such as an aptamer may form its structure before finding its complementary strand. The resulting affinity handles can be used for selective capture by IMAC or other techniques.

Separation of Restriction Fragments

The invention can be used to separate restriction fragments without using agarose gels. This separation from desired insert fragments can be enhanced by the deliberate construction of repetitive complementary regions within a vector to facilitate a selective conformational change in the undesired backbone fragments. This technique also includes the deliberate introduction of "overhangs" in the restriction fragments to facilitate selective binding and capture.

Removal of Non-Supercoiled Plasmid Isoforms from Supercoiled Plasmid DNA

By using the selective denaturation/renaturation technique described above, the invention can be used to remove plasmid isoforms such as linear and open-circular (ocDNA) from supercoiled plasmid. Because of differing thermodynamic properties, the linear and ocDNA will exhibit thermodynamic properties which will allow it to be selectively denatured, thus exposing affinity handles in the form of exposed bases. The isoforms can then be removed by a suitable affinity method as described in this document.

Removal of Contaminating Genomic DNA from Recombinant Taq Polymerase or Other Proteins or Products This invention can be used in the manufacture of recombinant Taq polymerase or similar products that are sensitive to host genomic DNA contamination. For example, by introducing affinity handles in irreversibly denatured genomic DNA during purification of the Taq polymerase, the genomic DNA can be removed by a capture method such as IMAC without affecting the product.

DESCRIPTION OF DRAWINGS

FIG. 1 shows schematically removal of *E. coli* genomic DNA from pCMVsport-β-gal. Lane 1 is a supercoiled DNA ladder. Lane 2 is a pCMVsport-β-gal sample (20 μg) spiked with 8 μg *E. coli* genomic DNA (30% by weight genomic DNA) in 20 mM HEPES (heating buffer). Lane 3 is the sample from lane 2 heated at 80° C. for 1 minute followed by flash cooling with an equal volume of 20 mM HEPES, 500 mM NaCl (quenching buffer). Lane 4 is the sample in lane 3 after four batch bindings with Cu (II)-IDA matrix (IMAC).

FIG. 2: shows schematically Predicted Secondary Structure of anti-VEGF aptamer.

FIG. 3: shows schematically a graphical Representation of Aptamer Purification Using Introduction of Affinity Handles Followed by Affinity Capture. A vector containing the desired aptamer sequence is restricted using the appropriate enzymes. The mixture containing the sense-aptamer/antisense aptamer plus vector backbone is then denatured via heat, alkali or other methods and quickly returned to native conditions to induce a conformational change in the aptamer and anti-sense strand. The desired material can be captured by passing the mixture through an affinity column selective for the desired aptamer strand. The aptamer is then eluted off the column using the appropriate eluent.

FIG. 4 shows schematically a General Purification Scheme for Introduction of Affinity Handles Followed by Affinity Capture Using Heating and Quenching Followed by an Affinity Column. The sample is first passed through a heating loop of appropriate length to denature the sample. The sample is next quenched with second buffer stream (top of figure) or passed through a second coil to rapidly cool the sample (bottom of figure). The rapidly quenched sample is then passed through an affinity column.

EXAMPLES

Example 1

Selective Thermal Denaturation and Renaturation with Capture of Genomic DNA to Yield Plasmid DNA In this example, plasmid DNA was prepared as follows: *E. coli* JM109 harboring the plasmid pCMVsport β-gal (7.9 kb, Gibco BRL) was cultured on LB medium containing kanamycin (50 μg/ml). Shake flasks (4 L, containing 1 L LB) were incubated with shaking at 37° C. overnight, and cell mass was harvested by centrifugation at 1000×g for 30 min and frozen at −80° C. Frozen cells (10 grams) were suspended in 100 ml of 25 mM Tris, 10 mM EDTA, pH 8.0. The pellet was vigorously stirred at 4° C. for 30 minutes to ensure complete re-suspension, which is essential for efficient lysis. The plasmid was extracted using alkaline lysis followed by purification using selective spermidine compaction precipitation. Plasmid purity was verified by electrophoresis at 16 V/cm in 1×TAE buffer on a 0.8% agarose gel containing SYBR gold (Molecular Probes). Final plasmid and genomic DNA concentrations were determined using a Beckman DU 7500 spectrophotometer with unit absorbance at 260 nm corresponding to 50 μg DNA ml$^{-1}$.

Cu(II)-IDA beads (IMAC beads) were prepared as follows: chelating Sepharose FF® (Amersham) was washed three times with Milli-Q® grade water, then charged on a Roto-Torque® rotator (Cole-Palmer) with 50 mM $CuCl_2$ (Acros) for one hour. Before use, the beads were washed three times with water, then three times with 20 mM HEPES, 250 mM NaCl, pH 7.0.

For selective binding of genomic DNA in the presence of plasmid, samples containing a mixture of pCMVsport β-gal and *E. coli* genomic DNA were prepared in 20 mM HEPES (no NaCl) as described above. The 50 μL sample was heated at 80° C. for 1 minute and then flash cooled with one volume (50 μL) of room temperature 20 mM HEPES, 500 mM NaCl. This sample (100 μL) was then added to 50 μL of settled Cu (II)-IDA-agarose slurry and incubated at room temperature on a rotator for one hour. The supernatant was next transferred to an identical fresh tube of Cu (II)-IDA and equilibrated for one hour. This process was repeated twice more. The final supernatant was collected for electrophoresis and qPCR analysis. The Cu (II)-IDA beads in both samples were washed and then eluted with 0.5 M imidazole in 20 mM HEPES, 250 NaCl buffer overnight.

For *E. coli* genomic DNA quantitation, the Stratagene MX 4000 was used to carry out qPCR experiments. A TaqMan® probe sequence ((6FAM)-CCCCGTACACAAAAATGCA-CATGCTG-(6TAMRA); SEQ ID NO:1) and primer set sequences (5'-GAAAGGCGCGCGATACAG-3' (SEQ ID NO:2) and 3'-GTCCCGCCCTACTCATCGA-5' (SEQ ID NO:3)) targeting the 7-copy *E. coli* 23S rRNA gene were used. Qiagen's HotStarTaq MasterMix® PCR reagents were used and the optimal primer ratio for the reaction was found to be 5:1 (forward:reverse). A standard curve was constructed between 100 fg and 1 ng of *E. coli* genomic DNA to quantitate the final genomic DNA concentrations in experimental samples. The PCR cycle used was: 15 min at 95° C.; (12 min at 94° C.; 1 min at 60° C.)×40.

A yield of about ninety percent (90%) recovery of the total plasmid DNA in its desired supercoiled form has been observed using selective thermal denaturation and renaturation with IMAC.

Example 2

Alkaline Denaturation

A sample (20 μL) containing a mixture of pCMVsport β-gal and *E. coli* genomic DNA was prepared as described above in Example 1. 1.4 μL of a 1 M NaOH solution was added and thoroughly mixed to bring the sample to a pH of 12.3 (predicted by titration of 20 mM HEPES). The sample was incubated at room temperature for 5 minutes followed by addition of 1.9 μL of 0.5 M HCl, 2 M NaCl solution while mixing to rapidly neutralize the sample. This sample was then added to 12 μL of settled Cu (II)-IDA-agarose slurry and incubated at room temperature on a rotator for one hour. The supernatant was next transferred to an identical fresh tube of Cu (II)-IDA and equilibrated for one hour. This process was repeated twice more. The final supernatant was collected for analysis by electrophoresis. The results obtained were similar to Example 1.

Example 3

Purification of an Anti-VEGF Aptamer from Restriction Fragments Using IMAC with Ammonium Chloride Elution The sequence of the desired aptamer (5'CCG TCT TCC AGA CAA GAG TGC AGG G 3') is inserted into a plasmid (or other suitable vector) along with its double stranded partner and expressed in the desired host organism. Following standard DNA purification and endonuclease restriction, the mixture is prepared in 20 mM HEPES buffer with no added NaCl. The mixture is heated for 1 minute at 80° C. followed by rapid addition of one volume of 20 mM HEPES, 500 mM NaCl in order to stabilize the aptamer in its stem-loop form (FIG. 2). The sample is quickly loaded on to a Cu(II) charged IMAC column to bind the single stranded regions of the structured aptamer and its complementary strand. After binding, a gradient of Ammonium Chloride ($NH_3Cl$) or other suitable eluent from 0 to 500 mM is passed through the column in order to selectively separate the vector backbone and the two strands from each other. For a continuous purification scheme, the setup(s) in FIG. 4 can be used.

Example 4

Purification of an Anti-VEGF Aptamer from Restriction Fragments Using an Oligonucleotide Affinity Column The experiment proceeds as in Example 3 with the exception of the affinity column used. To capture the desired aptamer after introduction of affinity handles, an affinity column is used that has immobilized oligonucleotides complementary to a single stranded region of the desired aptamer (e.g. 3' ACA GTC CCC 5'). The heated and quenched mixture is passed over the affinity column, selectively capturing the desired aptamer product. The product can then be eluted by a strong chaotropic salt, heat, or with low-salt buffer.

Example 5

Purification of DNA-Free Recombinant Taq Polymerase

A vector expressing Taq polymerase is harbored in an *E. coli* strain and grown on the appropriate medium in batch or continuous mode. The cells are harvested after 15-18 hours and lysed via mechanical disruption in the presence of lysis buffer (20 mM HEPES, 0.5% Brij 58). The lysate is clarified to remove particulate material and cell debris. The clarified lysate is then heated at 80° C. for 1 minute followed by quenching in an equal volume of high salt buffer (20 mM HEPES, 500 mM NaCl). The mixture is then passed over an IMAC column charged with Cu(II) to remove contaminating nucleic acids, including denatured *E. coli* genomic DNA. Standard protein purification steps are then carried out to isolate the Taq polymerase from other proteins in the lysate. A scheme like FIG. 4 can be used for continuous removal of genomic DNA.

Table A shows preferred values for some of the parameters of the invention.

TABLE A

| Parameter | Preferred | More Preferred | Most Preferred |
|---|---|---|---|
| Product | Nucleic Acid, Recombinant Protein, carbohydrate | Oligonucleotides, Circular DNA constructs, Structured RNA | Supercoiled Plasmid DNA, BACs, PACs, YACs |
| Contaminant | Nucleic Acids, rRNA | Oligonucleotide sense or anti-sense strand, Open circular/linear plasmid DNA, Host DNA | Host DNA (Genomic) |
| Affinity Handle | Single strandedness, double strandedness, Triplexes, Stem or loop structures (hairpin), Cruciform structures | Single strandedness in nucleic acids, hydrophobicity, hydrophilicity | Exposed base-pairs on host genomic DNA |
| Separation Step | Affinity capture | Immobilized oligonucleotides (specific or non), Immobilized SSB protein, Immobilized metals, minerals, metal affinity precipitation, metal affinity electrophoresis, pyrimidine-selective IMAC | Purine-selective IMAC with various metals |
| Separation format | Spin column, magnetic beads, filter plate, chromatography column, electrophoresis, microwell plate | Chromatography column, magnetic beads | Filter plate |
| Denaturation Step | Chaotropic Agents | Urea, Guanidine Hydrochloride/Thiocyanate, pH (low or high) | Thermal, Alkali pH |
| Thermal Denaturation temp/pH | 40-110° C./ **8-14 | 50-110° C./10-13 pH | 60-100° C./ 11-12.5 pH |
| gDNA level after purification | Undetectable by electrophoresis or qPCR | less than 20 picograms/microgram plasmid DNA | less than 8 picograms gDNA per microgram of Plasmid DNA |

MODIFICATIONS

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein.

Also it will be obvious to skilled persons that products and/or separation step techniques than other those recited herein may be used to great advantage in specific applications of the invention.

Reference to documents made in the specification is intended to result in such patents or literature being expressly incorporated herein by reference.

What is claimed is:

1. A method for separating a polymerase from nucleic acid in a sample comprising:
   treating the sample to expose purine bases present in the nucleic acid by a process selected from the group consisting of thermal denaturation, alkaline denaturation and restriction enzyme digestion yielding single-stranded overhangs;
   capturing the exposed purine bases of the nucleic acid on a metal chelate matrix, wherein the polymerase does not bind the metal chelate matrix;
   separating the polymerase from the metal chelate matrix; and
   recovering the polymerase, thereby separating the polymerase from the nucleic acid.

2. The method of claim 1 wherein the polymerase is a thermostable polymerase.

3. The method of claim 2 wherein the polymerase is Taq polymerase.

4. The method of claim 1 wherein the nucleic acid is genomic DNA.

5. The method of claim 1 wherein the sample is a cell lysate.

6. The method of claim 1 wherein the separation is achieved using multi-channel plates.

7. The method of claim 1 wherein the separation is achieved using magnetic particles.

8. The method of claim 1 wherein multiple samples are treated in parallel fashion.

9. The method of claim 1 wherein the metal chelate matrix comprises Cu(II).

10. The method of claim 1 wherein exposing is performed by thermal denaturation followed by quenching in a salt buffer.

11. The method of claim 10 wherein the salt buffer comprises 20 mM HEPES and 500 mM NaCl.

12. The method of claim 1 wherein exposing is performed by thermal denaturation followed by cooling.

* * * * *

SEQUENCE LISTING

```
<160> NUMBER OF SEQ ID NOS: 4

<210> SEQ ID NO 1
<211> LENGTH: 26
<212> TYPE: DNA
<213> ORGANISM: Escherichia coli
<220> FEATURE:
<221> NAME/KEY: misc_feature
<222> LOCATION: (1)..(1)
<223> OTHER INFORMATION: modified by FFAM dye
<220> FEATURE:
<221> NAME/KEY: misc_feature
<222> LOCATION: (26)..(26)
<223> OTHER INFORMATION: modified by 6TAMRA dye

<400> SEQUENCE: 1
ccccgtacac aaaaatgcac atgctg                                          26

<210> SEQ ID NO 2
<211> LENGTH: 18
<212> TYPE: DNA
<213> ORGANISM: Artificial Sequence
<220> FEATURE:
<223> OTHER INFORMATION: TaqMan probe

<400> SEQUENCE: 2
gaaaggcgcg cgatacag                                                   18

<210> SEQ ID NO 3
<211> LENGTH: 19
<212> TYPE: DNA
<213> ORGANISM: Artificial Sequence
<220> FEATURE:
<223> OTHER INFORMATION: primer sequence

<400> SEQUENCE: 3
gtcccgccct actcatcga                                                  19

<210> SEQ ID NO 4
<211> LENGTH: 26
<212> TYPE: DNA
<213> ORGANISM: Artificial Sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: 6FAM dye
<220> FEATURE:
<221> NAME/KEY: misc_feature
<222> LOCATION: (26)..(26)
<223> OTHER INFORMATION: modified by 6TAMRA

<400> SEQUENCE: 4
ccccgtacac aaaaatgcac atgctg                                          26
```